US012629404B2

(12) United States Patent
Corvari et al.

(10) Patent No.: US 12,629,404 B2
(45) Date of Patent: *May 19, 2026

(54) GIP/GLP1 AGONIST COMPOSITIONS

(71) Applicant: ELI LILLY AND COMPANY,
Indianapolis, IN (US)

(72) Inventors: Vincent John Corvari, Carmel, IN
(US); Christopher Sears Minie,
Zionsville, IN (US); **Dinesh Shyamdeo
Mishra, Carmel, IN (US); Ken Kangyi
Qian**, Carmel, IN (US)

(73) Assignee: ELI LILLY AND COMPANY,
Indianapolis, IN (US)

( * ) Notice: Subject to any disclaimer, the term of this
patent is extended or adjusted under 35
U.S.C. 154(b) by 0 days.

This patent is subject to a terminal dis-
claimer.

(21) Appl. No.: 19/379,195

(22) Filed: Nov. 4, 2025

(65) Prior Publication Data

US 2026/0053888 A1     Feb. 26, 2026

Related U.S. Application Data

(63) Continuation of application No. 19/042,887, filed on
Jan. 31, 2025, now Pat. No. 12,453,756, and a
continuation of application No. 19/276,978, filed on
Jul. 22, 2025, which is a continuation of application
No. 19/042,887, filed on Jan. 31, 2025, now Pat. No.
12,453,756, which is a continuation of application
No. 18/422,177, filed on Jan. 25, 2024, now Pat. No.
12,453,755, which is a continuation of application
No. 17/741,067, filed on May 10, 2022, now Pat. No.
11,918,623, which is a continuation of application
No. 16/441,329, filed on Jun. 14, 2019, now Pat. No.
11,357,820.

(60) Provisional application No. 62/688,632, filed on Jun.
22, 2018.

(51) Int. Cl.
*A61K 38/00* (2006.01)
*A61K 9/00* (2006.01)
*A61K 38/16* (2006.01)
*A61K 47/02* (2006.01)
*A61K 47/10* (2017.01)
*A61M 5/20* (2006.01)

(52) U.S. Cl.
CPC ............ *A61K 38/16* (2013.01); *A61K 9/0019*
(2013.01); *A61K 47/02* (2013.01); *A61K 47/10*
(2013.01); *A61M 5/20* (2013.01)

(58) Field of Classification Search
CPC ........ A61K 38/16; A61K 47/02; A61K 47/10;
A61K 9/0019; A61K 38/26; A61K
9/0021; A61M 5/20; A61P 3/10
See application file for complete search history.

(56) References Cited

U.S. PATENT DOCUMENTS

| | | | |
|---|---|---|---|
| 7,084,243 B2 | 8/2006 | Glaesner et al. | |
| 7,498,308 B2 | 3/2009 | Glaesner et al. | |
| 8,114,833 B2 | 2/2012 | Pedersen et al. | |
| 8,734,394 B2 | 5/2014 | Adams et al. | |
| 9,474,780 B2 | 10/2016 | Bokvist et al. | |
| 11,357,820 B2 * | 6/2022 | Corvari ................. | A61K 38/16 |
| 11,918,623 B2 * | 3/2024 | Corvari ................. | A61K 38/16 |
| 12,453,755 B2 * | 10/2025 | Corvari ................. | A61K 38/16 |
| 12,453,756 B2 * | 10/2025 | Corvari ................. | A61K 38/16 |
| 2009/0232807 A1 | 9/2009 | Glaesner et al. | |
| 2010/0196405 A1 | 8/2010 | Ng | |
| 2012/0329708 A1 | 12/2012 | DiMarchi et al. | |
| 2017/0136092 A1 | 5/2017 | Arnold et al. | |

FOREIGN PATENT DOCUMENTS

| | | |
|---|---|---|
| CN | 103893744 B | 12/2017 |
| EP | 0619322 A2 | 10/1994 |
| WO | 2003002136 A2 | 1/2003 |
| WO | 2004105790 A1 | 12/2004 |
| WO | 2006051103 A2 | 5/2006 |
| WO | 2006051110 A2 | 5/2006 |
| WO | 2008019147 A2 | 2/2008 |
| WO | 2011094337 A1 | 8/2011 |
| WO | 2013164483 A1 | 11/2013 |
| WO | 2014005858 A1 | 1/2014 |
| WO | 2014166836 A1 | 10/2014 |
| WO | 2014202780 A1 | 12/2014 |
| WO | 2015022400 A1 | 2/2015 |
| WO | 2015071355 A1 | 5/2015 |
| WO | 2015104311 A1 | 7/2015 |
| WO | 2018103868 A1 | 6/2018 |

OTHER PUBLICATIONS

Fransson, J., & Espander-Jansson, A. (1996). Local tolerance of
subcutaneous injections. Journal of pharmacy and pharmacology,
48(10), 1012-1015.
Williamson, A .; Hoggart,(2005)Pain: A review of three commonly
used pain rating scales. Journal of Clinical Nursing, 14, (7), 798-
804).
Millican, R.L., et al, Diabetes, Suppl., Abstract Book, A363 1504-P,
65th Scientific Sessions, NY col. 54 (Jun. 2005).
Laursen, T., Hansen, B., & Fisker, S. (2006). Pain perception after
subcutaneous injections of media containing different buffers. Basic
& clinical pharmacology & toxicology, 98(2), 218-221.
Troy, Editor, (2006) Remington: The Science and Practice of
Pharmacy (21st edition Lippincott Williams & Wilkins) https://
books.google.com/books?isbn=0781746736.
Saha, J. K., Xia, J., Millican, R., Grondin, J. M., Glaesner, W., &
Jakubowski, J. A. (2007). DPP-4 Resistant Glucagon-Like Peptide-1
Analog LY548806: A Novel Agent for Control of Acute Hypergly-
cemia.
Chandra Mohan, Buffers, A guide for the preparation and use of
buffers in biological systems, Calbiochem, 38 pages, EMD booklet
2014.

(Continued)

*Primary Examiner* — Lianko G Garyu
*Assistant Examiner* — Mercy H Sabila
(74) *Attorney, Agent, or Firm* — Parker D. McCrary

(57) ABSTRACT

A composition of tirzepatide, comprising an agent selected
from NaCl and propylene glycol; and dibasic sodium phos-
phate is provided.

32 Claims, No Drawings

Specification includes a Sequence Listing.

(56)                 References Cited

OTHER PUBLICATIONS

Product Description of Phosphate Buffered Saline, Smartbuffers, Medicago AB, 2 pages, 2010.
Phosphate Buffered Saline—Cold Harbor Protocols, 1 page, 2006.
Lachman, The Theory and Practice of Industrial Pharmacy, Varghese Publishing House, 11987, p. 190-193.
Aulton, The Science of Dosage Form Design, Pharmaceutics, Second Edition, 2002, p. 317.
Disodium Hydrogen Phosphate, Monograph, 2 pages.
Bydureon Prescribing Information, 2018, 49 pages.
Chabenne et al, J Diabetes Sci Technol, 2010, 4, 6, p. 1322-1331.
Selinsky, Membrane Protein Protocols, Methods in Molecular Biology, 2003, 228, 3 pages.
Larsen et al, Diabetes, 2001, 50, 11, p. 2530-3539.
Norregaard, et al, Diabetes Obes Metabl, 2018, 20 p. 60-68.
Frokjaer et al, Pharmaceutical Formulation Development of Peptides, 2000, pp. 124, 125, 150, 151.
Swarbrick, Encylopedia of Pharmaceutical Technology, vol. 1, 3rd Edition, 2007, p. 1266-1278.
Gibson, Pharmaceutical Preformulation and Formulation, 2009, 2nd ed, p. 325-328.
FDA Highlights of Prescribing Information Ozempic, 2017, 44 pages.
FDA Highlights of Prescribing Information Victoza, 2017, 40 pages.
Rowe, et al., Handbook of Pharmaceutical Excipients, 2009, 6th ed, p. 637-639.
Nema, et al., Pharmaceutical Dosage Forms, Formulation and Packaging, vol. 1, p. 232-237.
So, Improving Patient Compliance with Biopharmaceuticals by Reducing Injection-Associated Pain, Journal of Mucopolysaccharidosis and Rare Diseases, 2015, p. 15-18.
Coskun et al, Molecular Metabolism, 2018, 18, 3-14.
Cleland et al, Formulation and Delivery of Proteins and Peptides, 1994, Chapter 1, 19 pages.
Saxenda—Prescribing Information, 2014, 40 pages.
Yu et al, Advanceed Drug Del Rev, 2018, 130, 113-130.
Tresiba Prescribing Instructions, 2018, 35 pages.
Egrifta Prescribing Instructions, 2015, 21 pages.
Wang and Hanson, Jo Parenteral Science and Technology, 1988, 42, 2S, S4-S25.
Chang et al, Lypophilized Biologics and Vaccines, Lypophilized Biologics, 2016, p. 93-119.
Arturk et al, Jo of Diabetes Science and Technology, 2024, p. 1-5.
EP Opposition of EP3810201—Preliminary Opinion, 2025, 9 pages.

* cited by examiner

SEQUENCE LISTING

```
Sequence total quantity: 1
SEQ ID NO: 1           moltype = AA   length = 39
FEATURE                Location/Qualifiers
SITE                   2
                       note = X at position 2 is Aib
SITE                   13
                       note = X at position 13 is Aib
MOD_RES                20
                       note = Lys at position 20 is chemically modified through
                        conjugation to the epsilon-amino group of the K side-chain
                        with
                        (2-[2-(2-Amino-ethoxy)-ethoxy]-acetyl)2-(gamma-Glu)1-CO-(CH
                        2)18-CO2H
MOD_RES                39
                       note = Ser at position 39 is amidated as a C-terminal
                        primary amide
source                 1..39
                       mol_type = protein
                       organism = synthetic construct
SEQUENCE: 1
YXEGTFTSDY SIXLDKIAQK AFVQWLIAGG PSSGAPPPS                      39
```

GIP/GLP1 AGONIST COMPOSITIONS

REFERENCE TO AN ELECTRONIC SEQUENCE LISTING

The present application is being filed along with a Sequence Listing in ST.26 XML format. The Sequence Listing is provided as a file titled "X21660C_US.xml" created Jan. 28, 2025, and is 4,000 bytes in size. The Sequence Listing information in the ST.26 XML format is incorporated herein by reference in its entirety.

The present invention is a pharmaceutical GIP/GLP1 co-agonist peptide composition for subcutaneous injection. The composition comprises tirzepatide, NaCl, and dibasic sodium phosphate. The composition provides commercially acceptable shelf-life stability, in-use stability, and is associated with acceptable patient injection site experience. An alternative composition comprises tirzepatide, propylene glycol, and dibasic sodium phosphate that also provides acceptable shelf-life stability.

Diabetes mellitus is a chronic disorder characterized by hyperglycemia resulting from defects in insulin secretion, insulin action, or both. In type 2 diabetes mellitus ("T2D"), the combined effects of impaired insulin secretion and insulin resistance are associated with elevated blood glucose levels. Tirzepatide is a GIP/GLP1 co-agonist peptide useful in the treatment of diabetes. Tirzepatide is useful in the treatment of obesity.

U.S. Pat. No. 9,474,780 generally describes compositions containing a GIP/GLP1 agonist, administered by parenteral routes. U.S. Pat. No. 9,474,780 describes and claims tirzepatide. There is a desire for compositions of tirzepatide providing acceptable stability and acceptable patient injection site experience.

The present invention seeks to meet these needs by providing pharmaceutically-acceptable compositions of tirzepatide, or a pharmaceutically acceptable salt thereof; comprising an agent selected from the group consisting of NaCl and propylene glycol; and dibasic sodium phosphate.

In an embodiment, the agent is NaCl. In an embodiment, the NaCl concentration is from about 6.2 mg/mL to about 9.5 mg/mL. In an embodiment the NaCl concentration is from about 7.0 mg/mL to about 9.0 mg/mL. In an embodiment, the NaCl concentration is about 8.2 mg/mL.

In an embodiment, the agent is propylene glycol. In an embodiment, the propylene glycol concentration is from about 12.0 mg/mL to about 18.0 mg/mL. In an embodiment the propylene glycol concentration is from about 14.0 mg/mL to about 16.0 mg/mL. In an embodiment, the propylene glycol concentration is about 15.0 mg/mL.

In an embodiment, the dibasic sodium phosphate concentration is from about 0.67 mg/mL to about 2.68 mg/mL. In an embodiment, the dibasic sodium phosphate is about 1.0 mg/mL to about 3.0 mg/mL. In an embodiment, the dibasic sodium phosphate is about 1.34 mg/mL.

In an embodiment, the tirzepatide concentration is from about 5 mg/mL to about 30 mg/mL and the agent is NaCl. In an embodiment, the tirzepatide concentration is from about 10 mg/mL to about 30 mg/mL. In an embodiment, the tirzepatide concentration is from about 5 mg/mL to about 30 mg/mL; the NaCl concentration is about 8.2 mg/mL, and dibasic sodium phosphate concentration is from about 0.67 mg/mL to about 2.68 mg/mL. In an embodiment, the tirzepatide concentration is from about 5 mg/mL to about 30 mg/mL; the NaCl concentration is about 8.2 mg/mL, dibasic sodium phosphate concentration is from about 0.67 mg/mL to about 2.68 mg/mL, and the composition is presented in a single use automatic injection apparatus.

In an embodiment, the tirzepatide concentration is from about 5 mg/mL to about 30 mg/mL; and the agent is propylene glycol. In an embodiment, the tirzepatide is from about 5 mg/mL to about 30 mg/mL; the propylene glycol is from about 12.0 mg/mL to about 18.0 mg/mL, and the dibasic sodium phosphate concentration is about 1.34 mg/mL. In an embodiment, the tirzepatide concentration is from about 5 mg/mL to about 30 mg/mL; the propylene glycol is about 15.0 mg/mL, and the dibasic sodium phosphate concentration is about 1.34 mg/mL.

In an embodiment, the tirzepatide concentration is from about 5 mg/mL to about 30 mg/mL. In certain embodiments, the tirzepatide concentration is from about 10 mg/mL to about 30 mg/mL. In an embodiment the tirzepatide concentration is selected from the group consisting of 5, 10, 15, 20, 25, and 30 mg/mL. In an embodiment, 0.5 mL or less of the composition is administered as a dose. In an embodiment, the tirzepatide concentration is selected from the group consisting of 10, 20, and 30 mg/mL.

In an embodiment, the tirzepatide composition further comprises a preservative. In an embodiment, the tirzepatide composition comprises tirzepatide, dibasic sodium phosphate, propylene glycol, and a preservative. In an embodiment, the preservative is selected from the group consisting of metacresol and phenol. In an embodiment, the metacresol concentration is from about 2.0 mg/mL to about 4.0 mg/mL. In an embodiment the metacresol concentration is from about 3.0 mg/mL to about 3.5 mg/mL. In an embodiment, the metacresol concentration is about 3.15 mg/mL. In an embodiment, the phenol concentration is from about 3.0 mg/mL to about 7.0 mg/mL. In an embodiment the phenol concentration is from about 4.0 mg/mL to about 6.0 mg/mL. In an embodiment, the phenol concentration is about 5.0 mg/mL. In an embodiment, a tirzepatide composition is provided wherein tirzepatide concentration is from about 5 mg/mL to about 30 mg/mL; propylene glycol concentration is from about 12.0 mg/mL to about 18.0 mg/mL; dibasic sodium phosphate concentration is from about 0.67 to about 2.68 mg/mL; and metacresol concentration is from about 2.0 mg/mL to about 4.0 mg/mL. In an embodiment, the metacresol concentration is about 3.15 mg/mL. In an embodiment, a tirzepatide composition is provided wherein tirzepatide concentration is from about 5 mg/mL to about 30 mg/mL; propylene glycol concentration is from about 12.0 mg/mL to about 18.0 mg/mL; dibasic sodium phosphate concentration is from about 0.67 to about 2.68 mg/mL; and phenol concentration is from about 3.0 mg/mL to about 7.0 mg/mL. In an embodiment, a tirzepatide composition is provided wherein tirzepatide concentration is from about 5 mg/mL to about 30 mg/mL; propylene glycol concentration is from about 12.0 mg/mL to about 18.0 mg/mL; dibasic sodium phosphate concentration is from about 0.67 to about 2.68 mg/mL; and phenol concentration is about 5.0 mg/mL.

In an embodiment, the dose of a tirzepatide composition is administered about once weekly. In an embodiment, the dose of a tirzepatide composition is administered once every seven days.

In an embodiment, there is provided a method of treating diabetes comprising administering to a human in need thereof an effective dose of one of the above-described compositions.

In an embodiment, there is provided a method of treating obesity comprising administering to a human in need thereof an effective dose of one of the above-described compositions. In an embodiment, there is provided a method of providing therapeutic weight loss comprising administering to a human in need thereof an effective dose of one of the above-described compositions. In an embodiment, there is provided a method of treating a condition mediated by GIP/GLP1 co-agonist activity comprising administering to a human in need thereof an effective dose of one of the above-described compositions.

In an embodiment, there is provided one of the above-described compositions for use as a medicament.

In an embodiment, there is provided one of the above-described compositions for use in the treatment of diabetes. In an embodiment, there is provided one of the above-described compositions for use in the treatment of obesity.

In an embodiment, there is provided one of the above-described compositions for use in providing therapeutic weight loss. In an embodiment, there is provided one of the above-described compositions for use in providing non-therapeutic weight loss.

According to another aspect of the present invention, there is provided an article of manufacture comprising one of the above-described compositions. In certain embodiments, the article of manufacture is a multi-use vial. In certain embodiments, the article of manufacture is a pre-filled syringe. In certain embodiments, the article of manufacture is an automatic injection apparatus ("auto-injector"). An example of an auto-injector, as contemplated herein, is presented in U.S. Pat. No. 8,734,394.

As used herein, "tirzepatide" means a GIP/GLP1 co-agonist peptide as described in U.S. Pat. No. 9,474,780 and described by CAS Registry Number: 2023788-19-2. Tirzepatide is described in Example 1 of U.S. Pat. No. 9,474,780, with the following sequence:

$$YX_1EGTFTSDYSIX_2LDKIAQKAFVQWLIAGGPSSGAPPPS$$

wherein $X_1$ is Aib; $X_2$ is Aib; K at position 20 is chemically modified through conjugation to the epsilon-amino group of the K side-chain with (2-[2-(2-Amino-ethoxy)-ethoxy]-acetyl)$_2$-($\gamma$Glu)$_1$-CO—(CH$_2$)$_{18}$—CO$_2$H; and the C-terminal amino acid is amidated as a C-terminal primary amide (SEQ ID NO: 1).

When used herein, "pharmaceutically acceptable salt" is well known to the skilled artisan. In an embodiment is a pharmaceutically acceptable salt that is a tirzepatide trifluoroacetate salt.

When used herein, the term "does not contain a surfactant" means that the composition contains no added surfactant agents, or contains only a de minimis quantity of an added surfactant.

When used herein the term "propylene glycol" is well known to the skilled artisan. Propylene glycol is also represented by the formula: $C_3H_8O_2$.

The compositions of the present invention have concentrations of tirzepatide 30 between 5 mg/mL and 30 mg/mL. The compositions of the present invention are likely to have specific concentrations of 5, 10, 15, 20, 25, and 30 mg/mL. Such compositions may be presented in a pre-filled syringe. Such pre-filled syringe may be useful for administering one half milliliter of such composition per patient per dose. A dose of tirzepatide composition may be administered using a dosing schedule determined by a physician.

The compositions are sterile when first produced. If provided in a multi-use vial or cartridge, an anti-microbial preservative compound or mixture of compounds that is compatible with the other components of the composition may be added at sufficient strength to meet applicable regulatory anti-microbial preservative requirements. Pharmaceutically acceptable preservatives are well-known in the art. (See, e.g., Remington: The Science and Practice of Pharmacy (D. B. Troy, Editor, 21$^{st}$ Edition, Lippincott, Williams & Wilkins, 2006). In an embodiment, the preservative is meta-cresol. In an embodiment, the preservative is phenol. A composition for single use pre-filled syringe requires no preservative. In an embodiment, the composition does not contain a surfactant.

The pH of tirzepatide compositions of the present invention is typically 6.5 to 7.5 and it is adjusted using physiologically appropriate acids and bases, as may be required to achieve the desired pH. In an embodiment, the pH target is between 6.7 and 7.3. Patient injection site experience is a consideration for a subcutaneously administered composition. It is desirable to select a composition associated with an acceptable patient injection site experience. For example, NaCl and citrate have been associated with painful stinging at the injection site. (Laursen, T.; Hansen, B.; Fisker, S. Pain perception after subcutaneous injections of media containing different buffers. *Basic & Clinical Pharmacology & Toxicology* 2006, 98, (2), 218-221.), (Fransson, J.; Espander-Jansson, A. Local tolerance of subcutaneous injections. *Journal of Pharmacy and Pharmacology* 1996, 48, (10), 1012-1015.) It is further desirable to match the tonicity (i.e., osmolality) of body fluids at the injection site as closely as possible when administering the compositions because solutions that are not approximately isotonic with body fluids can produce a painful stinging sensation when administered. It is desirable that the compositions be approximately isotonic with body fluids at the sites of injection. The present composition comprising tirzepatide, NaCl, and dibasic sodium phosphate is associated acceptable patient injection site experience. Likewise, the composition comprising tirzepatide, proplylene glycol, and dibasic sodium phosphate is associated with acceptable patient injection site experience.

In an embodiment, the pH is adjusted using a base to facilitate dissolution in the buffer solution. The addition of an acid to the composition may be required to adjust the pH to the desired pH range. In an embodiment, NaOH is used to facilitate dissolution of tirzepatide in a buffer. In an embodiment, HCl is added to adjust the pH of the composition containing the dissolved tirzepatide to the desired pH range.

The compositions of the present invention are typically administered subcutaneously. The compositions are typically administered using a pre-filled, disposable pen, reusable pen, or automatic pen injector. The composition may be administered using a multi-use vial or a pump device. In an embodiment, the device is an automatic injection apparatus as claimed by U.S. Pat. No. 8,734,394.

A composition comprising tirzepatide, NaCl, and dibasic sodium phosphate provides a desired shelf life stability and provides patients with an acceptable injection site experience. Likewise, a composition comprising tirzepatide, propylene glycol, and dibasic sodium phosphate provides a desired shelf life stability and provides patients with an acceptable injection site experience. As used herein, "shelf life stability" is measured under controlled conditions at about 5 degrees Celsius. A composition comprising tirzepatide, NaCl, and dibasic sodium phosphate provides acceptable in-use stability. Likewise, a composition comprising tirzepatide, propylene glycol, and dibasic sodium phosphate provides acceptable in-use stability. As used herein, the term "in-use stability" refers to the stability of the composition measured under controlled conditions at or about 25 degrees Celsius or at or about 40 degrees Celsius.

Example #1—Composition Containing NaCl

The composition is prepared substantially as described herein. The compositions containing 5, 10, 15, 20, 15, and 30 mg/mL of tirzepatide each contain the ingredients set forth in Table 1. Acid or base is optionally added to attain the desired pH range. Water is added *quantum satis* (q. s.) to one milliliter total final volume.

TABLE 1

| Formulation of Tirzepatide, Phosphate, and NaCl | |
| --- | --- |
| Ingredient | Concentration (mg/mL) |
| Tirzepatide | 5, 10, 15, 20, 25, and 30 |
| dibasic sodium phosphate* | 1.34 |
| NaCl | 8.2 |

*5 mM.phosphate buffer is used

Example #2—Composition Containing Propylene Glycol

The composition is prepared substantially as described herein. The compositions providing 5, 10, 15, 20, 15, and 30 mg/mL compositions of tirzepatide each contain the ingredients set forth in Table 2. Acid or base is optionally added to attain the desired pH range. Water is added *quantum satis* to one milliliter total final volume.

TABLE 2

| Formulation of Tirzepatide, Phosphate, and Propylene Glycol | |
| --- | --- |
| Ingredient | Concentration (mg/mL) |
| Tirzepatide | 5, 10, 15, 20, 25, and 30 |
| dibasic sodium phosphate* | 1.34 |
| Propylene glycol | 15 |

*5 mM phosphate buffer is used

Size Exclusion Chromatography (SEC) in-Use Stability Study

This procedure is an isocratic size exclusion HPLC method with UV detection at 214 nm and is designed to determine the relative amounts of tirzepatide monomer and total aggregates. Monomer and aggregates are reported as peak area percent to the total area. The procedure is stability indicating as measured by its ability to resolve known impurities from tirzepatide. This study compares alternate compositions with the compositions of this invention, prepared as shown by Table 3. The stability from this study is shown in Table 4.

TABLE 3

| Stability study comparing alternate compositions: | | | | |
| --- | --- | --- | --- | --- |
| | | Formulation | | |
| Ingredient | Control | NaCl | Mannitol | Glycerol |
| Tirzepatide (mg/mL) | 2 | 2 | 2 | 2 |
| Sodium phosphate dibasic 7H$_2$O (mg/mL)** | 2.68 | 2.68 | 2.68 | 2.68 |

TABLE 3-continued

| Stability study comparing alternate compositions: | | | | |
| --- | --- | --- | --- | --- |
| | | Formulation | | |
| Ingredient | Control | NaCl | Mannitol | Glycerol |
| NaCl (mg/mL) | — | 8.8 | — | — |
| Mannitol (mg/mL) | — | — | 45 | — |
| Glycerol (mg/mL) | — | — | — | 27 |
| Water (mg/mL) | q.s. to 1 mL | q.s. to 1 mL | q.s. to 1 mL | q.s. to 1 mL |

**10 mM phosphate buffer is used

TABLE 4

| Tirzepatide monomer (% peak area) by size-exclusion chromatography (SEC) | | | | | |
| --- | --- | --- | --- | --- | --- |
| | Temp | | Time (month) | | |
| Composition | (° C.) | 0 | 0.5 | 1 | 2 |
| Control | 25 | 98.25 | 98.15 | 97.76 | 96.63 |
| (Table 3) | 40 | | 97.62 | 95.80 | 93.19 |
| NaCl | 25 | 98.23 | 98.13 | 97.95 | 97.47 |
| (Table 3) | 40 | | 97.84 | 97.28 | 96.22 |
| Mannitol | 25 | 98.23 | 97.87 | 97.39 | 95.17 |
| (Table 3) | 40 | | 96.72 | 92.71 | 83.48 |
| Glycerol | 25 | 98.25 | 98.11 | 97.77 | 96.62 |
| (Table 3) | 40 | | 97.36 | 94.51 | 84.11 |

Shelf Life Stability Study

RP-HPLC:

This procedure is a gradient reversed-phase HPLC method with UV detection at 214 nm and is designed to determine the quantity, identity, and purity of tirzepatide in the drug product. Identity is determined by matching the retention time of the main peak with that of the main peak of an external reference standard. Quantity is determined by the comparison of the main peak area with the corresponding peak in the external reference standard. Impurities and related substances are reported as peak area percent to the total peak area. The procedure is stability indicating as judged by its ability to resolve known impurities from tirzepatide. As shown by Table 4, a composition comprising NaCl as a tonicity agent provides acceptable in-use stability.

Size Exclusion Chromatography (SEC) Shelf-Life Stability Study

The size exclusion stability study methods and RP-HPLC described herein above are applied to compare compositions comprising NaCl as a tonicity and stabilizing agent with compositions comprising propylene glycol as a tonicity and stabilizing agent. This study illustrates the acceptable shelf-life stability of a composition of this invention comprising NaCl agent or comprising propylene glycol as agent. The compositions used for this study are set forth in Table 5. The stability from this study is shown in Table 6.

TABLE 5

| Comparison between NaCl and propylene glycol | | |
| --- | --- | --- |
| Ingredient | Formulation of NaCl as agent | Formulation of Propylene glycol as agent |
| Tirzepatide (mg/mL) | 20 | 20 |
| Sodium phosphate dibasic 7H$_2$O (mg/mL)* | 1.34 | 1.34 |

TABLE 5-continued

Comparison between NaCl and propylene glycol

| Ingredient | Formulation of NaCl as agent | Formulation of Propylene glycol as agent |
|---|---|---|
| NaCl (mg/mL)) | 8.8 | — |
| Propylene glycol (mg/mL) | — | 15 |
| Water | q.s. to mL | q.s. to mL |

*5 mM phosphate buffer is used in the study

TABLE 6

Comparison of NaCl to Propylene Glycol as an agent in Tirzepatide formulations by determining monomer (% peak area) by SEC and purity by RP-HPLC

| Composition | Temp (° C.) | 0 | 1 | 2 | 3 |
|---|---|---|---|---|---|
| | | | Time (month) | | |
| Monomer by SEC | | | | | |
| NaCl | 5 | 99.35 | — | — | 98.81 |
| (Table 5) | 30 | | 97.20 | 98.03 | 97.79 |
| Propylene glycol | 5 | 98.51 | 98.20 | | |
| (Table 5) | 30 | | 97.94 | | |
| Purity by RP-HPLC | | | | | |
| NaCl | 5 | 92.87 | — | — | 95.95 |
| (Table 5) | 30 | | 91.70 | 90.40 | 89.26 |
| Propylene glycol | 5 | 93.38 | 93.31 | | |
| (Table 5) | 30 | | 92.04 | | |

Pain Upon Injection Study:

All compositions are prepared as described by Table 7. Each solution composition vial is held at room temperature about 30 minutes, but not more than four hours. Reconstituted lyophilized compositions are used immediately. All injections are rotated between the 4 quadrants of the abdomen, in the following order; lower left quadrant; lower right quadrant; upper left quadrant; and upper right quadrant. A syringe with a 29 gauge needle is used to administer the composition from a vial. A fold of skin at the injection site is grasped by the subject, and the needle is inserted at about a 45 degree angle. A second person uses a stop watch to measure the length of time of injection. The subject slowly pushes the plunger of the syringe all the way until 0.5 mL of the composition is injected. The target time of injection is 4 seconds duration, and not more than 5 seconds. The needle is removed from the skin after injection and skin is released from the subject's grasp. The subject immediately assesses the pain after each injection. Pain measurements are assessed using a 100-mm validated visual analog scale (VAS) for pain. The VAS is a well-validated tool to assess injection-site pain (Williamson, A.; Hoggart, B. Pain: A review of three commonly used pain rating scales. *Journal of Clinical Nursing* 2005, 14, (7), 798-804). The VAS is presented as a 10-cm (100-mm) line, anchored by verbal descriptors, usually "no pain" and "worst imaginable pain." The subject is asked to mark the 100-mm line to indicate pain intensity at time points and as clinically indicated. A staff member uses a caliper to measure the distance from 0 to the mark that the subject placed on the VAS, and to record the measurement in the source document. Results from this study appear in Table 8. An acceptable patient injection site experience is reflected by a mild pain intensity indication (compared to moderate or severe).

TABLE 7

| Compositions for Pain Intensity Study.Ingredient | Formulation of NaCl | Formulation of Propylene glycol |
|---|---|---|
| Tirzepatide (mg/mL) | 20 | 20 |
| Sodium phosphate dibasic 7H$_2$O (mg/mL)* | 1.34 | 1.34 |
| NaCl (mg/mL)) | 8.8 | — |
| Propylene glycol (mg/mL) | — | 15 |
| Water | q.s. to mL | q.s. to mL |

| Ingredient | Placebo of NaCl as agent | Placebo of Propylene glycol as agent |
|---|---|---|
| Tirzepatide (mg/mL) | 0 | 0 |
| Sodium phosphate dibasic 7H$_2$O (mg/mL)* | 1.34 | 1.34 |
| NaCl (mg/mL)) | 8.8 | — |
| Propylene glycol (mg/mL) | — | 15 |
| Water | q.s. to mL | q.s. to mL |

| Ingredient | Formulation of NaCl as agent-Lyophilized |
|---|---|
| Tirzepatide (mg/mL) | 20 |
| Sodium phosphate dibasic 7H$_2$O (mg/mL)* | 1.34 |
| NaCl (mg/mL)) | 8.8 |
| Propylene glycol (mg/mL) | — |
| Water: sterile water for injection- reconstitute; swirl to dissolve | q.s. to mL |

*5 mM phosphate buffer is used in the study

TABLE 8

VAS pain score.

| Composition (per Table 7) | Pain intensity | | |
|---|---|---|---|
| | Mild (VAS: 0 mm-30 mm) | Moderate (VAS: 31 mm-70 mm) | Severe (VAS: 71 mm-100 mm) |
| Tirzepatide lyophilized, reconstituted | 90% | 5% | 5% |
| Tirzepatide composition propylene glycol | 100% | 0% | 0% |
| Tirzepatide composition NaCl | 100% | 0% | 0% |
| Placebo composition NaCl | 100% | 0% | 0% |
| Placebo composition propylene glycol | 100% | 0% | 0% |

Tirzepatide

SEQ ID NO: 1

YX$_1$EGTFTSDYSIX$_2$LDKIAQKAFVQWLIAGGPSSGAPPPS wherein X$_1$ is Aib; X$_2$ is Aib; K at position 20 is chemically modified through conjugation to the epsilon-amino group of the K side-chain with (2-[2-(2-Amino-ethoxy)-ethoxy]-acetyl)$_2$-($\gamma$Glu)$_1$-CO—(CH$_2$)$_{18}$—CO$_2$H; and the C-terminal amino acid is amidated as a C-terminal primary amide

We claim:

1. A pharmaceutical composition comprising:

(a) tirzepatide, or a pharmaceutically acceptable salt thereof; and (b) from about 6.2 mg/mL to about 9.5 mg/mL of sodium chloride (NaCl), wherein the pharmaceutical composition has a pH of from about 6.5 to about 7.5 and the composition is free of preservative.

2. The pharmaceutical composition of claim 1, wherein the composition comprises from about 7.0 mg/mL to about 9.0 mg/mL of NaCl.

3. The pharmaceutical composition of claim 2, wherein the composition comprises about 8.2 mg/mL of NaCl.

4. The pharmaceutical composition of claim 1, wherein the composition has a pH of from about 6.7 to about 7.3.

5. The pharmaceutical composition of claim 1, wherein the composition comprises from about 5 mg/mL to about 30 mg/mL of tirzepatide, or a pharmaceutically acceptable salt thereof.

6. The pharmaceutical composition of claim 5, wherein the composition comprises 5 mg/mL, 10 mg/mL, 15 mg/mL, 20 mg/mL, 25 mg/mL, or 30 mg/mL of tirzepatide, or a pharmaceutically acceptable salt thereof.

7. The pharmaceutical composition of claim 1, wherein the composition is administered using a pre-filled syringe, a pre-filled pen, or an automatic injection apparatus.

8. The pharmaceutical composition of claim 1, wherein the composition is in a vial.

9. The pharmaceutical composition of claim 6, wherein the composition comprises about 8.2 mg/mL of NaCl.

10. The pharmaceutical composition of claim 9, wherein the composition comprises dibasic sodium phosphate at a concentration of from about 0.67 mg/mL to about 2.68 mg/mL.

11. The pharmaceutical composition of claim 10, wherein the composition is administered using a pre-filled syringe, a pre-filled pen, or an automatic injection apparatus.

12. The pharmaceutical composition of claim 10, wherein the composition is in a vial.

13. A pharmaceutical composition comprising:

(a) tirzepatide, or a pharmaceutically acceptable salt thereof;

(b) from about 6.2 mg/mL to about 9.5 mg/mL of NaCl; and (c) dibasic sodium phosphate, wherein the composition is free of preservative.

14. The pharmaceutical composition of claim 13, wherein the composition comprises from about 7.0 mg/mL to about 9.0 mg/mL of NaCl.

15. The pharmaceutical composition of claim 14, wherein the composition comprises about 8.2 mg/mL of NaCl.

16. The pharmaceutical composition of claim 13, wherein the dibasic sodium phosphate concentration is from about 1 mg/mL to about 3 mg/mL.

17. The pharmaceutical composition of claim 13, wherein the dibasic sodium phosphate concentration is from about 0.67 mg/mL to about 2.68 mg/mL.

18. The pharmaceutical composition of claim 17, wherein the dibasic sodium phosphate concentration is about 1.34 mg/mL.

19. The pharmaceutical composition of claim 13, wherein the composition comprises 5 mM of dibasic sodium phosphate.

20. The pharmaceutical composition of claim 13, wherein the composition comprises from about 5 mg/mL to about 30 mg/mL of tirzepatide, or a pharmaceutically acceptable salt thereof.

21. The pharmaceutical composition of claim 17, wherein the composition comprises 5 mg/mL, 10 mg/mL, 15 mg/mL, 20 mg/mL, 25 mg/mL, or 30 mg/mL of tirzepatide, or a pharmaceutically acceptable salt thereof.

22. The pharmaceutical composition of claim 13, wherein the composition is administered using a pre-filled syringe, a pre-filled pen, or an automatic injection apparatus.

23. The pharmaceutical composition of claim 13, wherein the composition is in a vial.

24. The pharmaceutical composition of claim 13, wherein the pharmaceutical composition has a pH of from about 6.5 to about 7.5.

25. The pharmaceutical composition of claim 21, wherein the pharmaceutical composition has a pH of from about 6.5 to about 7.5.

26. The pharmaceutical composition of claim 25, wherein the composition comprises about 8.2 mg/mL of NaCl.

27. The pharmaceutical composition of claim 26, wherein the composition is administered using a pre-filled syringe, a pre-filled pen, or an automatic injection apparatus.

28. The pharmaceutical composition of claim 26, wherein the composition is in a vial.

29. A method for treating type-2 diabetes comprising administering to a human in need thereof an effective dose of the pharmaceutical composition of claim 1.

30. A method for treating obesity comprising administering to a human in need thereof an effective dose of the pharmaceutical composition of claim 1.

31. A method for treating type-2 diabetes comprising administering to a human in need thereof an effective dose of the pharmaceutical composition of claim 13.

32. A method for treating obesity comprising administering to a human in need thereof an effective dose of the pharmaceutical composition of claim 13.

\* \* \* \* \*